(12) United States Patent
Yang

(10) Patent No.: US 9,834,484 B1
(45) Date of Patent: *Dec. 5, 2017

(54) PLANT ENHANCER AND A METHOD OF USING THE SAME

(71) Applicant: GLUCAN BIOLOGICAL TECHNOLOGY CO., LTD, Irvine, CA (US)

(72) Inventor: Junbo Yang, Nanjing (CN)

(73) Assignee: GLUCAN BIOLOGICAL TECHNOLOGY CO., LTD, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,738

(22) Filed: May 8, 2017

(30) Foreign Application Priority Data

May 24, 2016 (CN) .......................... 2016 1 0347813

(51) Int. Cl.
| | |
|---|---|
| *A01N 59/16* | (2006.01) |
| *C05F 11/00* | (2006.01) |
| *C05G 3/00* | (2006.01) |
| *C05F 17/00* | (2006.01) |

(52) U.S. Cl.
CPC .............. *C05F 11/00* (2013.01); *A01N 59/16* (2013.01); *C05F 17/0081* (2013.01); *C05G 3/00* (2013.01)

(58) Field of Classification Search
None
See application file for complete search history.

(56) References Cited

U.S. PATENT DOCUMENTS 4,812,159 A * 3/1989 Freepons ............... A01N 43/16
47/57.6

FOREIGN PATENT DOCUMENTS

CN           102775755 B   * 12/2013

OTHER PUBLICATIONS

Yuan et al., Inorg. Chem., 2007, 46, 5302-5309.*

* cited by examiner

*Primary Examiner* — Abigail Vanhorn
(74) *Attorney, Agent, or Firm* — SZDC Law P.C.

(57) ABSTRACT

A plant enhancer includes a ferrocenyl polymer composition, a polyaryl ether nitrile-carbonyl iron magnetic material, silica nanoparticles, and an amino acid powder.

10 Claims, No Drawings

PLANT ENHANCER AND A METHOD OF USING THE SAME

The present invention claims priority to Chinese Patent Application No. 201610347813.7, filed on May 24, 2016, which is incorporated by reference for all purposes as if fully set forth herein.

FIELD OF THE INVENTION

The present invention relates to a plant enhancer and a method of using the same.

BACKGROUND OF THE INVENTION

Magnetic material is the basis for the emerging cluster of functional materials. As early as 3,000 years ago, China had discovered that magnets attract each other and ion, used magnet for direction and correcting time. These applications only involve natural magnets. The study of the performance characteristics of magnetic materials, manufacturing, and applications started less than 100 years ago. After nearly a century, the magnetic materials have formed a large family, according to the magnetic properties of the materials, including soft magnetic material, permanent magnetic material, rotating magnetic material, magnetic memory, pressure magnetic material. The magnetic materials also include magnetic alloy material and ferrite magnetic material. In recent years, a new magnetic materials emerged—organic polymer magnetic material, which is a major breakthrough in the field of polymer materials. Organic polymer magnetic material is believed to be one of the most important scientific discoveries in the 1980s. Its discovery can be compared with superconductivity and solid organic superconductor. Organic polymer magnetic material can lead a series of new technologies.

β-glucan is a new health product. It can be used to treat obesity, to reduce cholesterol, to lower blood sugar, to prevent cardiovascular disease, and to improve immunity.

β-glucan exists mainly in fresh foods, such as brewer's yeast, oats, and edible fungi. It is a polysaccharide, and its main chemical structure is β-1,3-dextran and β-1,6-dextran. β-1,3-dextran has anti-tumor properties, improves body's immune system, and acts as a prebiotic to adjust the intestinal flora structure.

*Ganoderma* is known as a cure for all diseases and an immortality herb. The main reason is that *ganoderma* is rich in β-glycan. In 1963, β-glycan was first discovered that β-glycan has anti-tumor activity. β-glycan was then also found to have antibacterial activities and be effective in treating hepatitis, cardiovascular, diabetes, high blood lipids, and aging. Chinese Ministry of Health listed β-glucan as a new resource food in Bulletin No. 9 in 2010.

β-glucan is effective in treating diabetes and cancer and enhancing immunity. It mechanism is as follows.

The mechanism of treating diabetes: β-glucan has a special ultra-helical molecular structure, a strongest and most immunologically active form easily absorbed by the body. It will not be hydrolyzed in the gastrointestinal tract into glucose and other simple sugars, and therefore diabetic patients will not be affected by taking β-glucan. β-glucan can lower blood glucose of type II diabetes patients, stimulate insulin secretion, improve insulin sensitivity, reduce insulin resistance, and promote liver glycogen, muscle glycogen synthesis, having significant improvement in glucose tolerance.

The mechanism of treating cancer: when β-glucan enter into body, it binds to a specific receptor and enters the lymphatic system by endocytosis (or pinocytosis) through the intestinal epithelium. Some studies show that β-glucan inhibits more than 95% tumor growth.

Mechanism of enhancing immunity: β-glucan has a triple helical structure with unique targeting characteristics, and is active against locked dormancy, drug resistance and subclinical disease virus. β-glucan also quickly activates the body's own immune surveillance and identification of mechanisms to maintain a healthy body.

There is a need to increase β-glucan production. Currently, the above-mentioned magnetic organic polymer has not been used to increase β-glucan production.

SUMMARY OF THE INVENTION

In one embodiment, the present invention provides a plant enhancer. The plant enhancer includes a ferrocenyl polymer composition, a polyaryl ether nitrile-carbonyl iron magnetic material, silica nanoparticles, and an amino acid powder.

In another embodiment, a content of the ferrocenyl polymer composition is 20-100 parts by weight, a content of the polyaryl ether nitrile-carbonyl iron magnetic material is 20-100 parts by weight, a content of the silica nanoparticles are 2-10 parts by weight, and a content of the plant-based amino acid powder is 20-80 parts by weight.

In another embodiment, the content of the ferrocenyl polymer composition is 50-80 parts by weight, the content of the polyaryl ether nitrile-carbonyl iron magnetic material is 50-80 parts by weight, the content of the silica nanoparticles are 6-8 parts by weight, and the content of the plant-based amino acid powder is 50-60 parts by weight.

In another embodiment, the ferrocenyl polymer composition includes a polymer selected from the group consisting of a ferrocenyl oxime polymer, a ferrocenyl hydrazone polymer, and a ferrocenyl amide polymer; and a rare earth metal salt.

In another embodiment, the rare earth metal salt is a lanthanum salt, a scandium salt, a yttrium salt, a praseodymium salt, or a holmium salt.

In another embodiment, the amino acid powder is a plant-based amino acid powder.

In one embodiment, the present invention provides a method of growing a plant. The method includes applying the plant enhancer.

In another embodiment, the plant is a food crop, a cash crop, a vegetable crop, a fruit, and a fodder crop.

In another embodiment, the plant enhancer is mixed with a fertilizer in an amount of 1 to 5 wt % of the fertilizer.

In another embodiment, the silica nanoparticles have an average particle size of 20-30 nm.

In another embodiment, the silica nanoparticles have an average particle size of 30 nm.

The advantages of the present invention include: the combination of a ferrocenyl polymer composition, a polyaryl ether nitrile-carbonyl iron magnetic material, silica nanoparticles, and an amino acid powder magnetizes chemical fertilizers, pesticides and feed molecules, catalyzes the decomposition of chemical fertilizers, pesticides and feed molecules, improves the utilization of chemical fertilizers, pesticides and feed molecules, stimulates plant growth and the accumulation of plant nutrient molecules, and increases the production of β-glucan in the plant.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

The present invention provides a plant enhancer. The plant enhancer includes a ferrocenyl polymer composition, a polyaryl ether nitrile-carbonyl iron magnetic material, silica nanoparticles, and an amino acid powder. The preparation of the plant enhancer and the method of using the plant enhancer are described in details.

Silica nanoparticles 30 nm ($SiO_2$, amorphous, purity: 99.9%, Average Particle Size (APS): 30 nm, SSA: 440 $m^2/g$, color: white, morphology: spherical, bulk density: 0.063 $g/cm^3$, true density: 2.2-2.6 $g/cm^3$) was purchased from Beijing DK Nano technology Co., Ltd. Plant-based amino acid powder (light yellow powder or granule; components: AA≥40%; ASP 2.21%, THR 2.06%, SER 2.73%, GLU 5.33%, GLY 1.40%, ALA 1.38%, CYS 1.07%, VAL 1.88%, MET 0.27%, ILE 1.10%, IEU 1.43%, TYR 0.42%, PHE 0.97%, LYS 1.16%, HIS 0.30%, ARG 2.98%, PRD 2.28%) was purchased from Chengdu Chelation Biology Technology Co., Ltd.

Example 1

A plant enhancer includes 20 parts by weight (hereafter "parts") of ferrocenyl polymer composition, 20 parts of polyaryl ether nitrile-carbonyl iron magnetic material, 2 parts of silica nanoparticles, and 20 parts of plant-based amino acid powder.

The preparation of the ferrocenyl polymer composition: under high purity nitrogen protection, 5 parts of ferrocenyl oxime polymer was mixed with 8 parts of lanthanum sulfate in a reaction tube. DMSO was added to the mixture, and the mixture was then stirred at 155° C. for 12 hours. After the reaction was complete, the mixture was filtered, washed with hot water and ethanol, and dried under vacuum for 8 hours to obtain the ferrocenyl polymer composition.

The preparation of the polyaryl ether nitrile-carbonyl iron magnetic material: 100 parts of carbonyl iron power and 2 parts of phenol sulfonic acid (hardener or cross-linking agent) were added to 80 parts of molten phthalonitrile monomer. The mixture was heated at 200° C. for 10 minutes and then cooled to obtain surface modified carbonyl iron power. 80 parts of the surface modified carbonyl iron power (inorganic filler) was mixed with 20 parts of polyaryl ether nitrile to obtain the polyaryl ether nitrile-carbonyl iron magnetic material.

Example 2

A plant enhancer includes 100 parts of ferrocenyl polymer composition, 100 parts of polyaryl ether nitrile-carbonyl iron magnetic material, 10 parts of silica nanoparticles, and 80 parts of plant-based amino acid powder.

The preparation of the ferrocenyl polymer composition: under high purity nitrogen protection, 3 parts of ferrocenyl oxime polymer was mixed with 5 parts of scandium sulfate in a reaction tube. DMSO was added to the mixture, and the mixture was then stirred at 155° C. for 12 hours. After the reaction was complete, the mixture was filtered, washed with hot water and ethanol, and dried under vacuum for 8 hours to obtain the ferrocenyl polymer composition.

The preparation of the polyaryl ether nitrile-carbonyl iron magnetic material: 100 parts of carbonyl iron power and 2 parts of phenol sulfonic acid (hardener or cross-linking agent) were added to 80 parts of molten phthalonitrile monomer. The mixture was heated at 200° C. for 10 minutes and then cooled to obtain surface modified carbonyl iron power. 80 parts of the surface modified carbonyl iron power (inorganic filler) was mixed with 20 parts of polyaryl ether nitrile to obtain the polyaryl ether nitrile-carbonyl iron magnetic material.

Example 3

A plant enhancer includes 60 parts of ferrocenyl polymer composition, 60 parts of polyaryl ether nitrile-carbonyl iron magnetic material, 6 parts of silica nanoparticles, and 50 parts of plant-based amino acid powder.

The preparation of the ferrocenyl polymer composition: under high purity nitrogen protection, 5 parts of ferrocenyl oxime polymer was mixed with 7 parts of yttrium sulfate in a reaction tube. DMSO was added to the mixture, and the mixture was then stirred at 155° C. for 12 hours. After the reaction was complete, the mixture was filtered, washed with hot water and ethanol, and dried under vacuum for 8 hours to obtain the ferrocenyl polymer composition.

The preparation of the polyaryl ether nitrile-carbonyl iron magnetic material: 100 parts of carbonyl iron power and 2 parts of phenol sulfonic acid (hardener or cross-linking agent) were added to 80 parts of molten phthalonitrile monomer. The mixture was heated at 200° C. for 10 minutes and then cooled to obtain surface modified carbonyl iron power. 80 parts of the surface modified carbonyl iron power (inorganic filler) was mixed with 20 parts of polyaryl ether nitrile to obtain the polyaryl ether nitrile-carbonyl iron magnetic material.

Example 4

A plant enhancer includes 50 parts of ferrocenyl polymer composition, 50 parts of polyaryl ether nitrile-carbonyl iron magnetic material, 6 parts of silica nanoparticles, and 50 parts of plant-based amino acid powder.

The preparation of the ferrocenyl polymer composition: under high purity nitrogen protection, 5 parts of ferrocenyl oxime polymer was mixed with 7 parts of praseodymium sulfate in a reaction tube. DMSO was added to the mixture, and the mixture was then stirred at 155° C. for 12 hours. After the reaction was complete, the mixture was filtered, washed with hot water and ethanol, and dried under vacuum for 8 hours to obtain the ferrocenyl polymer composition.

The preparation of the polyaryl ether nitrile-carbonyl iron magnetic material: 100 parts of carbonyl iron power and 2 parts of phenol sulfonic acid (hardener or cross-linking agent) were added to 80 parts of molten phthalonitrile monomer. The mixture was heated at 200° C. for 10 minutes and then cooled to obtain surface modified carbonyl iron power. 80 parts of the surface modified carbonyl iron power (inorganic filler) was mixed with 20 parts of polyaryl ether nitrile to obtain the polyaryl ether nitrile-carbonyl iron magnetic material.

Example 4

A plant enhancer includes 80 parts of ferrocenyl polymer composition, 80 parts of polyaryl ether nitrile-carbonyl iron magnetic material, 8 parts of silica nanoparticles, and 60 parts of plant-based amino acid powder.

The preparation of the ferrocenyl polymer composition: under high purity nitrogen protection, 5 parts of ferrocenyl oxime polymer was mixed with 8 parts of holmium sulfate in a reaction tube. DMSO was added to the mixture, and the mixture was then stirred at 155° C. for 12 hours. After the reaction was complete, the mixture was filtered, washed with hot water and ethanol, and dried under vacuum for 8 hours to obtain the ferrocenyl polymer composition.

The preparation of the polyaryl ether nitrile-carbonyl iron magnetic material: 100 parts of carbonyl iron power and 2 parts of phenol sulfonic acid (hardener or cross-linking agent) were added to 80 parts of molten phthalonitrile monomer. The mixture was heated at 200° C. for 10 minutes and then cooled to obtain surface modified carbonyl iron power. 80 parts of the surface modified carbonyl iron power (inorganic filler) was mixed with 20 parts of polyaryl ether nitrile to obtain the polyaryl ether nitrile-carbonyl iron magnetic material.

Example 6

The plant enhancers of Examples 1-5 were mixed with plant fertilizer, and the mixtures were applied to grow food crops, cash crops, vegetable crops, fruit, and fodder crops.

Mixture of the plant enhancer of Example 1 and fertilizer (the plant enhancer is 1 wt % of the fertilizer) was applied to grow β-Glucans-rich rice. A test conducted by TUV Rheinland Greater China showed that the rice contains 11.2 grams of β-Glucans per 100 grams of rice.

Mixture of the plant enhancer of Example 2 and fertilizer (the plant enhancer is 1 wt % of the fertilizer) was applied to grow β-Glucans-rich corn. A test conducted by TUV Rheinland Greater China showed that the corn contains 13.1 grams of β-Glucans per 100 grams of corn.

Mixture of the plant enhancer of Example 3 and fertilizer (the plant enhancer is 1 wt % of the fertilizer) was applied to grow β-Glucans-rich wheat. A test conducted by TUV Rheinland Greater China showed that the wheat contains 10.9 grams of β-Glucans per 100 grams of wheat.

Mixture of the plant enhancer of Example and fertilizer (the plant enhancer is 1 wt % of the fertilizer) was applied to grow β-Glucans-rich straw. A test conducted by TUV Rheinland Greater China showed that the straw contains 10.8 grams of β-Glucans per 100 grams of straw.

Mixture of the plant enhancer of Example 5 and fertilizer (the plant enhancer is 1 wt % of the fertilizer) was applied to grow β-Glucans-rich tomato. A test conducted by TUV Rheinland Greater China showed that the tomato contains 11.6 grams of β-Glucans per 100 grams of tomato.

These β-glucan-rich products (rice, wheat, corn, tomatoes etc.) can adjust body-specific immunity, prevent and suppress tumor, improve glucose metabolism, reduce blood glucose levels, prevent diabetes, improve liver function, enhance immunity, prevent liver disease, reduce high blood lipids, adsorb cholesterol, and prevent thrombosis. They can also have anti-tumor and anti-radiation effects, strength human health, fight virus and fungal infections, promote wound healing on the skin, and repair sun damage and skin aging.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A plant enhancer comprising:
    a ferrocenyl polymer composition,
    a polyaryl ether nitrile-carbonyl iron magnetic material,
    silica nanoparticles, and
    an amino acid powder.

2. The plant enhancer of claim 1, wherein
    a content of the ferrocenyl polymer composition is 20-100 parts by weight of the plant enhancer,
    a content of the polyaryl ether nitrile-carbonyl iron magnetic material is 20-100 parts by weight of the plant enhancer,
    a content of the silica nanoparticles are 2-10 parts by weight of the plant enhancer, and
    a content of the plant-based amino acid powder is 20-80 parts by weight of the plant enhancer.

3. The plant enhancer of claim 1, wherein the ferrocenyl polymer composition comprises:
    a polymer selected from the group consisting of a ferrocenyl oxime polymer, a ferrocenyl hydrazone polymer, and a ferrocenyl amide polymer; and
    a rare earth metal salt.

4. The plant enhancer of claim 3, wherein the rare earth metal salt is a lanthanum salt, a scandium salt, a yttrium salt, a praseodymium salt, or a holmium salt.

5. The plant enhancer of claim 1, wherein the amino acid powder is a plant-based amino acid powder.

6. A method of growing a plant comprising applying the plant enhancer of claim 1.

7. The method of claim 6, wherein the plant is a food crop, a cash crop, a vegetable crop, a fruit, and a fodder crop.

8. The method of claim 6, wherein the plant enhancer is mixed with a fertilizer in an amount of 1 to 5 wt % of the fertilizer.

9. The plant enhancer of claim 1, wherein the silica nanoparticles have an average particle size of 20-30 nm.

10. The plant enhancer of claim 1, wherein the silica nanoparticles have an average particle size of 30 nm.

* * * * *